United States Patent [19]

McDonald et al.

[11] Patent Number: 5,441,963
[45] Date of Patent: Aug. 15, 1995

[54] POTENTIATION OF NMDA ANTAGONISTS

[75] Inventors: Ian A. McDonald, Loveland; Bruce M. Baron, Cincinnati, both of Ohio

[73] Assignee: Merrell Dow Pharmaceuticals, Cincinnati, Ohio

[21] Appl. No.: 987,091

[22] Filed: Dec. 7, 1992

Related U.S. Application Data

[63] Continuation of Ser. No. 811,203, Dec. 20, 1991, abandoned.

[51] Int. Cl.⁶ .................... A61K 31/47; A61K 31/60; A61K 31/62
[52] U.S. Cl. .................... 514/311; 514/159; 514/161; 514/312
[58] Field of Search ............... 514/159, 161, 192, 311, 514/312

[56] References Cited

U.S. PATENT DOCUMENTS

| | | | |
|---|---|---|---|
| 2,608,507 | 8/1952 | Miller | 514/192 |
| 5,026,700 | 6/1991 | Harrison et al. | 514/312 |

*Primary Examiner*—Marianne M. Cintins
*Assistant Examiner*—Kevin E. Weddington
*Attorney, Agent, or Firm*—J. Michael Dixon

[57] ABSTRACT

The present invention is directed to a composition and method for poteniating the therapeutic effects of a class of known NMDA antagonists.

4 Claims, No Drawings

POTENTIATION OF NMDA ANTAGONISTS

This is a continuation of application Ser. No. 07/811,203, filed Dec. 20, 1991, now abandoned.

The present invention is directed to a method for potentiating the activity of a known class of excitatory amino acid antagonists. A further aspect of the invention is directed to a new pharmaceutical composition containing these antagonists.

In accordance with the present invention, it has been discovered that probenecid will potentiate the activity of the following class of excitatory amino acid antagonists:

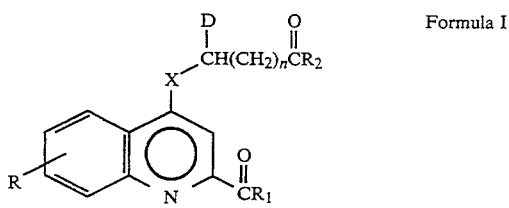

Formula I in which X is represented by NH; n is represented by an integer from 0 to 6; $R_1$ and $R_2$ are each independently represented by a substituent selected from the group consisting of $-NR_3R_4$, $-OH$, $-OR_5$, and $-OCH_2OCOR_6$ and, $-O-(CH_2)_p NR_7R_8$ in which p is an integer from 1-4; $R_3$ and $R_4$ are each independently represented by hydrogen or a $C_{1-6}$ alkyl; $R_5$ and $R_6$ are each independently represented by a $C_{1-6}$ alkyl, a phenyl ring, a substituted phenyl ring, or an alkylphenyl substituent in which the phenyl ring may be optionally substituted; $R_7$ and $R_8$ are independently represented by a $C_{1-6}$ alkyl or together with the adjacent nitrogen atom for a piperidino, morpholino, or pyrrolidinyl group; D is represented by hydrogen or a $C_{1-3}$ alkyl, and; R is represented by a substituent selected from the group consisting of hydrogen, OH, halogen, CN, $NO_2$, $C_{1-6}$ alkyl, $C_{1-6}$ alkoxy, $OCF_3$, $CF_3$, $COOR_3$, and $CONR_3R_4$ in which $R_3$ and $R_4$ are each independently as defined above; the pharmaceutically acceptable acid addition salts thereof, and the pharmaceutically acceptable basic addition salts thereof.

As used in this application:
a) the term "halogen" refers to a fluorine, chlorine, or bromine atom;
b) the terms "lower alkyl group and $C_{1-6}$ alkyl" refer to a branched or straight chained alkyl group containing from 1-6 carbon atoms, such as methyl, ethyl, n-propyl, isopropyl, n-butyl, isobutyl, n-pentyl, n-hexyl, etc;
c) the terms "lower alkoxy group and $C_{1-6}$ alkoxy" refer to a straight or branched alkoxy group containing from 1-6 carbon atoms, such as methoxy, ethoxy, n-propoxy, isopropoxy, n-butoxy, isobutoxy, n-pentoxy, n-hexoxy, etc.;
d) the term "substituted phenyl ring" refers to a phenyl ($C_6H_5$) which is substituted with up to 3 substituents, each substituent is independently selected from the group consisting of halogens, $C_{1-6}$ alkyl, $C_{1-6}$ alkoxy, $CF_3$, $OCF_3$, OH, CN, $NO_2$, $COOR_3$, and $CONR_3R_4$ in which $R_3$ and $R_4$ are represented by hydrogen or a $C_{1-6}$ alkyl. These substituents may be the same or different and may be located at any of the ortho, meta, or para positions.
e) the term "alkylphenyl substituent" refers to the following structure $-(CH_2)_m-C_6H_5$, in which m is an integer from 1-3. This phenyl ring may be substituted in the manner described immediately above.
f) the term "$C_{1-3}$ alkyl" refers to a straight or branched alkyl group containing from 1-3 carbon atoms such as methyl, ethyl, n-propyl, or isopropyl.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

In the compounds of Formula I, the quinoline ring may be substituted as indicated by the R substituent. When R is other than a hydrogen atom, there can be up to 3 such substituents occurring at any of positions 5, 6, 7, or 8 on the quinoline ring. These substituents can be the same or can differ. In the compounds of Formula I, $R_5$ and $R_6$ can be represented by either substituted phenyl rings or an alkylphenyl substituent in which the phenyl ring is substituted. These substituted phenyl rings may be substituted with up to 3 substituents. These substituents may be the same or different and may be located at any of the meta, para, or ortho positions.

The preferred compounds of Formula I are those in which R is a 5,7-dihalo substituent, $R_1$ and $R_2$ are OH, D is hydrogen and n is O. The most preferred compound is 4-carboxymethylamino-5,7-dichloro-2-quinoline carboxylic acid.

It has been discovered that probenecid will potentiate the therapeutic activity of the excitatory amino acid antagonists described by Formula I above (hereinafter the compounds). Thus the compounds of Formula I will exhibit their therapeutic effects at lower doses and for longer periods in patients who are concurrently receiving probenecid. The mechanism by which probenecid potentiates their effects is not fully understood, however it is believed that probenecid decreases the rate at which the compounds of Formula I are excreted from the central nervous system as well as decreasing their rate of excretion by the kidneys. Probenecid increases the effective concentration of these compounds in both the CNS and in the systemic circulation.

The compounds of Formula I, their method of preparation and their use as excitatory amino acid antagonists is described in U.S. Pat. No. 5,026,700 which is hereby incorporated by reference.

Probenecid is also known in the art. It is available commercially from Merck Sharp and Dohme under the tradename Benemid ® as well as being available from numerous other sources. Probenecid is a uricosuric agent and is utilized in the treatment of gout. Probenecid is a renal tubular transport blocking agent and has been utilized to increase plasma levels of penicillin. The pharmacology of probenicid is described in detail in the 45th Edition of the Physicians Desk reference on page 1379.

As noted above, the compounds of Formula I are excitatory amino acid antagonists. They antagonize the effects which excitatory amino acids have upon the NMDA receptor complex. They preferentially bind to the strychnine-insensitive glycine binding site located on the NMDA receptor complex. They are useful in the treatment of a number of disease states.

Ischemia, hypoglycemia, and trauma have been shown to raise extracellular concentrations of glutamate and aspartate to potentially neurotoxic levels. These antagonists will be neuroprotective in these and potentially other syndromes characterized by elevated glutamate and or aspartate concentrations. Thus the compounds are useful for preventing or minimizing the damage which nervous tissues contained within the CNS suffer upon exposure to either ischemic, hypoxic, traumatic or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, reduction of neuronal damage following trauma to the brain or spinal cord, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds exhibit anti-convulsant properties and are useful in the treatment of epilepsy. They are useful in the treatment of grand mal seizures, petit mal seizures, psychomotor seizures, and autonomic seizures. The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs. As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs. The compounds may also be utilized as anxiolytic agents and as analgesics. The therapeutic activity of these compounds is described in more detail in U.S. Pat. No. 5,026,700 which was incorporated by reference above.

The compounds of Formula I may be administered concurrently with probenecid in order to treat any of the diseases or conditions described above. The quantity of probenecid that is required to potentiate the therapeutic effects of the compounds of Formula I can vary widely depending upon the particular compound of Formula I being administered, the patient, and the presence of other underlying disease states within the patient, etc. Typically though, the probenecid may be administered at a dosage of from 0.5–3 g/day. Repetitive daily administration may be desirable and will vary according to the conditions outlined above. The probenecid will typically be administered from 2–4 times daily.

The dosage range at which the compounds of Formula I exhibit their effects can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg-day to about 500 mg/kg-day for any of the diseases or conditions listed above. With the concurrent administration of probenecid, this dosage range may be adjusted lower by a factor of 2 to 10 fold. Alternatively, the compounds of Formula I may be administered at the same dosage range in order to obtain an enhanced effect due to the higher therapeutic concentrations obtained. The dosage frequency of the compounds of Formula I can vary widely depending upon the condition or disease being treated. Repetitive daily administration may be desirable and will vary according to the conditions outlined above. For certain conditions such as stroke, it may be desirable to maintain a continuous IV infusion.

Probenecid is currently available commercially as tablets. The sodium salt of probenecid is readily water soluble and injectable dosage forms can be prepared from this salt using techniques well known to those skilled in the art.

The compounds of Formula I may be administered by a variety of routes. They are effective if administered orally. The compounds may also be administered parenterally (i.e. subcutaneously, intravenously, intramuscularly, intraperitoneally, or intrathecally). U.S. Pat. No. 5,026,700 teaches methods for preparing pharmaceutical dosage forms containing the compounds of Formula I.

The compounds of Formula I and probenecid can be administered as two different pharmaceutical dosage forms. Alternatively, in order to increase patient convience, the compounds of formula I and the probencid may be compounded into a single pharmaceutical dosage form. These pharmaceutical compositions can be manufactured utilizing techniques known in the art. Typically an antagonistic amount of the compound of Formula I and an effective amount of probenecid will be admixed with a pharmaceutically acceptable carrier.

For oral administration, the two medicaments can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the two medicaments can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredients in an aqueous or non-aqueous pharmaceutically acceptable solvent which may also contain suspending agents, sweetening agents, flavoring agents, and preservative agents as are known in the art.

For parenteral administration the two medicaments may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the medicaments are being administered intrathecally, they may also be dissolved in cerebrospinal fluid as is known in the art.

As used in this application:
  a) the term "patient" refers to warm blooded animals such as, for example, guinea pigs, mice, rats, cats, rabbits, dogs, monkeys, chimpanzees, and humans;
  b) the term "treat" refers to the ability of the compounds to either relieve, alleviate, or slow the progression of the patient's disease;
  c) the term "neurodegeneration" refers to a progressive death and disappearance of a population of nerve cells occurring in a manner characteristic of a particular disease state and leading to brain damage;
  d) the phrase "concurrent administration" refers to administering the probenicid at an appropriate time so that it will potentiate the antagonistic effects of the compounds of Formula I. This may means simultaneous administration or administration at appropriate but different times. Establishing such a proper dosing schedule will be readily apparent to one skilled in the art.

The following Examples are being presented in order to further illustrate the invention but they should not be construed as limiting the scope of the invention in any manner.

EXAMPLE I

The intracerebroventricular administration of quinolinic acid induces clonic seizures in mice. If a compound can inhibit the development of these seizures, it is considered to possess anti-epileptic activity. This example demonstrates the manner in which probenecid potentiated the ability of 4-carboxymethylamino-5,7-dichloro-2-quinoline carboxylic acid to inhibit the development of these seizures.

In this test, a group of ten mice were pretreated intravenously with 64 mg/kg of 4-carboxymethylamino-5,7-dichloro-2-quinoline carboxylic acid (hereinafter compound). Five minutes later the mice were administered 7.7 micrograms of quinolinic acid intracerebroventricularly in a volume of 5 microliters of saline. The animals were observed for 15 minutes thereafter for signs of clonic seizures. A second group of mice were subjected to the same test except that the mice were pretreated with the compound 30 minutes prior to the administration of quinolinic acid. The following results were obtained.

TABLE I

| PRETREATMENT TIME | # OF MICE PROTECTED | % PROTECTED |
|---|---|---|
| 5 minutes | 10/10 | 100 |
| 30 minutes | 1/10 | 10 |

In order to determine the effect of probenecid upon the antiepileptic effects of 4-carboxymethylamino-5,7-dichloro-2-quinoline carboxylic acid, the above test were repeated as above except that the mice were additionally pretreated with 200 mg/kg of probenecid-intraperitoneally at the indicated time. The following results were obtained.

TABLE II

| PRETREATMENT TIME | # OF MICE PROTECTED | % PROTECTED |
|---|---|---|
| 5 minutes | 10/10 | 100 |
| 30 minutes | 7/10 | 70 |

An examination of Tables I and II shows that the probenecid significantly extended the activity of the compound. Probenecid increased the effectiveness of 4-carboxymethylamino-5,7-dichloro-2-quinoline carboxylic acid in the 30 minute pretreatment group by a factor of 7.

EXAMPLE II

Another method for evaluating the anti-epileptic activity of selected compounds is by their ability to inhibit sound induced seizures in audiogenic mice. DBA/2J audiogenic mice experience seizures when exposed to loud noises. Compounds which prevent this phenomenon are considered to be antiepilpetic agents.

Groups of 4 to 8 DBA/2J audiogenic mice were administered i.p. 5 doses ranging from 1.5 to 200 mg/kg of 4-carboxymethylamino-5,7-dichloro-2-quinoline carboxylic acid (hereinafter compound). Five minutes after administration, they were placed individually in glass jars and exposed to a sound stimulus of 110 decibels for 30 seconds. Each mouse was observed during the sound exposure for signs of seizure activity. A graph was prepared based upon the dose administered and the percentage of animals protected from the seizures at that dose. An $ED_{50}$ was calculated from the graph. The test was then repeated twice, using naive animals, with the only modification being the addition of 100 mg/kg or 200 mg/kg of probenecid IP. The following $ED_{50}$'s were obtained.

TABLE III

| TREATMENT | $ED_{50}$ (mg/kg) |
|---|---|
| Compound | 131.8 |
| Compound + 100 mg/kg probenecid | 46.8 |
| Compound + 200 mg/kg probenecid | 10.8 |

Examination of the results obtained above in Table III demonstrates that probenecid significantly lowered the $ED_{50}$ of 4-carboxymethylamino-5,7-dichloro-2-quinoline carboxylic acid in this test.

What is claimed is:

1. A method for antagonizing the effects of excitatory amino acids upon the NMDA receptor complex comprising administering to a patient in need thereof, a compound of the formula:

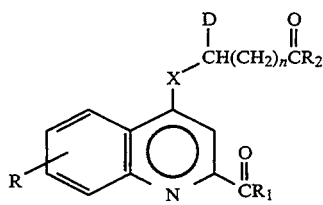

Formula I

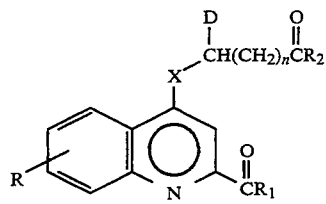

Formula I in which X is represented by NH; n is represented by an integer from 0 to 6; $R_1$ and $R_2$ are each independently represented by a substituent selected from the group consisting of $-NR_3R_4$, $-OH$, $-OR_5$, and $-OCH_2OCOR_6$ and, $-O-(CH_2)_p\ NR_7R_8$ in which p is an integer from 1-4; $R_3$ and $R_4$ are each independently represented by hydrogen or a $C_{1-6}$ alkyl; $R_5$ and $R_6$ are each independently represented by a $C_{1-6}$ alkyl, a phenyl ring, a substituted phenyl ring, or an alkylphenyl substituent in which the phenyl ring may be optionally substituted; $R_7$ and $R_8$ are independently represented by a $C_{1-6}$ alkyl or together with the adjacent nitrogen atom form a piperidino, morpholino, or pyrrolidinyl group; D is represented by hydrogen or a $C_{1-3}$ alkyl, and; R is represented by a substituent selected from the group consisting of hydrogen, OH, halogen, CN, $NO_2$, $C_{1-6}$ alkyl, $C_{1-6}$ alkoxy, $OCF_3$, $CF_3$, $COOR_3$, and $CONR_3R_4$ in which $R_3$ and $R_4$ are each independently as defined above; the pharmaceutically acceptable acid addition salts thereof, and the pharmaceutically acceptable basic addition salts thereof in an amount sufficient to antagonize the effects which excitatory amino acids have upon the NMDA receptor complex and probenecid in an amount sufficient to potentiate said antagonistic effects.

2. A method according to claim 1 in which said compound is 4-carboxymethylamino-5,7-dichloro-2-quinoline carboxylic acid.

3. A pharmaceutical composition comprising a compound of the formula:

in which X is represented by NH; n is represented by an integer from 0 to 6; $R_1$ and $R_2$ are each independently represented by a substituent selected from the group consisting of $-NR_3R_4$, $-OH$, $-OR_5$, $-OCH_2OCOR_6$ and, $-O-(CH_2)_p\ NR_7R_8$ in which p is an integer from 1-4; $R_3$ and $R_4$ are each independently represented by hydrogen or a $C_{1-6}$ alkyl; $R_5$ and $R_6$ are each independently represented by a $C_{1-6}$ alkyl, a phenyl ring, a substituted phenyl ring, or an alkylphenyl substituent in which the phenyl ring may be optionally substituted; $R_7$ and $R_8$ are independently represented by a $C_{1-6}$ alkyl or together with the adjacent nitrogen atom form a piperidino, morpholino, or pyrrolidinyl group; D is represented by hydrogen or a $C_{1-3}$ alkyl, and; R is represented by a substituent selected from the group consisting of hydrogen, OH, halogen, CN, $NO_2$, $C_{1-6}$ alkyl, $C_{1-6}$ alkoxy, $OCF_3$, $CF_3$, $COOR_3$, and $CONR_3R_4$ in which $R_3$ and $R_4$ are each independently as defined above; the pharmaceutically acceptable acid addition salts thereof, or the pharmaceutically acceptable basic addition salts thereof, present in an amount sufficient to antagonize the effects which excitatory amino acids have upon the NMDA receptor complex, in admixture with a pharmaceutically acceptable carrier and a sufficient amount of probenecid to potentiate said compound.

4. A pharmaceutical composition according to claim 3 in which said compound is 4-carboxymethylamino-5,7-dichloro-2-quinoline carboxylic acid.

* * * * *

UNITED STATES PATENT AND TRADEMARK OFFICE
CERTIFICATE OF CORRECTION

PATENT NO. : 5,441,963

DATED : August 15, 1995

INVENTOR(s) : Ian A. McDonald and Bruce M. Baron

It is certified that error appears in the above-identified patent and that said Letters Patent is hereby corrected as shown below:

At column 7, claim 1, line 21, the patent reads "$R_7$ and Re" and should read --$R_7$ and $R_8$-- .

Signed and Sealed this

Eighth Day of December, 1998

*Attest:*

BRUCE LEHMAN

*Attesting Officer*  Commissioner of Patents and Trademarks